US008263780B2

(12) United States Patent
Abele et al.

(10) Patent No.: US 8,263,780 B2
(45) Date of Patent: Sep. 11, 2012

(54) PROCESS FOR THE PREPARATION OF 2-IMINO-THIAZOLIDIN-4-ONE DERIVATIVES

(75) Inventors: Stefan Abele, Zurich (CH); Martin Bolli, Allschwil (CH); Gunther Schmidt, Aarau (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 152 days.

(21) Appl. No.: 12/516,055

(22) PCT Filed: Nov. 22, 2007

(86) PCT No.: PCT/IB2007/054752
§ 371 (c)(1),
(2), (4) Date: May 22, 2009

(87) PCT Pub. No.: WO2008/062376
PCT Pub. Date: May 29, 2008

(65) Prior Publication Data
US 2010/0317867 A1   Dec. 16, 2010
US 2011/0201821 A2   Aug. 18, 2011

(30) Foreign Application Priority Data

Nov. 23, 2006   (WO) ................. PCT/IB2006/054409

(51) Int. Cl.
*C07D 277/54*   (2006.01)
(52) U.S. Cl. ........................................ 548/184
(58) Field of Classification Search .................. 548/148
See application file for complete search history.

(56) References Cited

U.S. PATENT DOCUMENTS

| | | | | |
|---|---|---|---|---|
| 3,077,402 A * | 2/1963 | Blout et al. | ................... | 430/243 |
| 3,175,905 A | 3/1965 | Stahlhofen | | |
| 3,759,938 A | 9/1973 | Giraudon | | |
| 5,422,360 A * | 6/1995 | Miyajima et al. | ............. | 514/391 |
| 5,677,322 A * | 10/1997 | Yasumura et al. | ............ | 514/369 |
| 6,353,006 B1 * | 3/2002 | Dixon et al. | ................... | 514/338 |
| 6,380,229 B1 * | 4/2002 | Yoneda et al. | ................ | 514/369 |
| 7,435,828 B2 * | 10/2008 | Binkert et al. | ................ | 548/184 |
| 7,626,037 B2 * | 12/2009 | Binkert et al. | ................ | 548/184 |
| 7,767,701 B2 * | 8/2010 | Hasegawa et al. | ............ | 514/369 |
| 7,875,726 B2 * | 1/2011 | Binkert et al. | ................ | 548/184 |
| 2004/0009527 A1 * | 1/2004 | Dong et al. | .................... | 435/7.1 |
| 2004/0167192 A1 | 8/2004 | Solow-Cordero et al. | | |
| 2005/0019825 A9 * | 1/2005 | Dong et al. | .................... | 435/7.1 |
| 2007/0082933 A1 * | 4/2007 | Binkert et al. | ................ | 514/369 |
| 2007/0249599 A1 * | 10/2007 | Duffy et al. | ................ | 514/234.5 |
| 2008/0280962 A1 | 11/2008 | Binkert et al. | | |
| 2009/0275625 A1 | 11/2009 | Binkert et al. | | |
| 2011/0021581 A1 | 1/2011 | Brossard et al. | | |
| 2011/0196004 A1 | 8/2011 | Bonham et al. | | |

FOREIGN PATENT DOCUMENTS

| | | |
|---|---|---|
| EP | 1 219 612 A1 | 7/2002 |
| GB | 999796 | 7/1965 |
| WO | WO 91/17151 | 11/1991 |
| WO | WO 96/20936 A1 | 7/1996 |
| WO | WO 2004/007491 A1 | 1/2004 |
| WO | WO 2004/010987 | 2/2004 |
| WO | WO2005/054215 | 6/2005 |

OTHER PUBLICATIONS

Ottana et al., 5-Arylidene-2-imino-4-thiazolidinones: design and synthesis of novel anti-inflammatory agents, Biorganic & Medicinal Chemistry, 13(13) (2005) 4243-4252.
Klika, K.D., et al., "Regioselective Synthesis of 2-Imino-1,3-thiazolidin-4-ones by Treatment of N-(Anthracen-9-yl)-N9-ethylthiourea [. . . ]" Eur. J. Org. Chem. 2002, 1248-1255.
Erlenmeyer et al., CA 37:10142, 1943.
Ma, Tonghui, et al., "High-affinity Activators of Cystic Fibrosis Transmembrane Conductance Regulator (CFTR) Chloride Conductance Identified by High-throughout Screening", Journal of Biological Chemistry, vol. 277, No. 40, pp. 37235-37241. 2002.
Janusz, John M. et al., "New Cyclooxygenase-2/5-Lipoxygenase Inhibitors. 3. 7-tert-Butyl-2,3-dihydro-3,3-dimethylbenzofuran Derivatives as Gastronintestinal Safe Antiinflammatory and Analgesic Agents: Variations at the 5 Position", Journal of Medicinal Chemistry, vol. 41, 1998, pp. 3315-3529.
Carter, Percy H. et al., "Photochemically enhanced binding of small molecules to the tumor necrosis factor receptor-1 inhibits the binding of TNF-α", Proceedings of the National Academy of Sciences of the United States of America, vol. 98, No. 21, Oct. 9, 2001, pp. 11879-11884.
Berge, Stephen M. et al., "Pharmaceutical Salts", Journal of Pharmaceutical Sciences, vol. 66, No. 1, Jan. 1977, pp. 1-19.
Gould, Philip L. et al., "Salt selection for basic drugs", International Journal of Pharmaceutics, vol. 33, 1986, pp. 201-217.
Mark Gibson, Editor, Pharmaceutical Preformulation and Formulation, IHS Health Group, Englewood, CO, USA, 2001.
Remington, The Science and Practice of Pharmacy, 20th Edition, Philadelphia College of Pharmacy and Science, 2003.
U.S. Appl. No. 13/194,172, dated Jul. 29, 2011, Binkert, et al.
U.S. Appl. No. 13/205,768, dated Aug. 9, 2011, Binkert, et al.
Anonymous, "Actelion's Orally Active Selective S1P1 Receptor Agonist to be Jointly Developed/Promoted with Roche in Autoimmune Disorders and Transplantation Deal Potentially Worth Well Over US $630 Million to Actelion", Muscoskeletal Report, [Online], Jul. 20, 2006, pp. 1, New York, NY 10016, USA, Retrieved from the Internet: URL: http://www.mscreport.com/print.cfm?articleID=827>.
Bailer, et al., The New England Journal of Medicine, (1997), Massachusetts Medical Society, vol. 336, Issue 22, pp. 1569-1574.

(Continued)

*Primary Examiner* — Jason M Nolan
(74) *Attorney, Agent, or Firm* — Hoxie & Associates LLC

(57) ABSTRACT

The present invention relates to a new process for the preparation of 2-imino-thiazolidin-4-one compounds of the Formula (I) and (II) and to compounds of Formula (II) as such. The present compounds of Formula (II) can be used as intermediates in the preparation of thiazolidin-4-one derivatives of the General Formula (II), which thiazolidin-4-one derivatives being described in WO 2005/054215 to act as immunosuppressive agents.

4 Claims, No Drawings

OTHER PUBLICATIONS

Baker, Journal of Applied Physiology, (2002) American Physiological Society, vol. 92, pp. 177901780.

Beger, et al., World Journal of Surgery, (2003) Societe Internationale de Chirugie, vol. 27, pp. 1075-1084.

Braun-Moscovici, et al., Current Opinion in Rheumatology, (2002), Lippincott Williams and Wilkins, vol. 14, pp. 711-716.

Bunemann, M., et al., "Activation of Muscarinic $K^+$Current in Guinea-Pig Atrial Myocytes by Sphingosine-1-phosphate", Journal of Physiology, vol. 489, pp. 701-707, (1995).

Davidov, T., et al., "Chronic Nitric Oxide Synthase Blockade Desensitizes the Heart to the Negative Metabolic Effects of Nitric Oxide", Life Sciences, Pergamon Press, Oxford, GB, vol. 79, pp. 1674-1680, (2006).

Frolkis, V.V., "The Role of 'Invertors' (Intracellular Activators) in Age-related Changes in Cell Response to Hormones", Experimental Gerontology, vol. 30, pp. 401-414, (1995).

Fujishiro, J., et al., "Use of Sphingosine-1-Phosphate 1 Receptor Agonist, KRP-203, in Combination with a Subtherapeutic Dose of Cyclosporine A for Rat Renal Transplantation", Transplantation, vol. 82(6), pp. 804-812, (2006).

Giese, et al., Journal of Cancer Research and Clinical Oncology, (2001), Springer-Verlag, vol. 127, pp. 217-225.

Guo, J., et al., "Effects of Sphingosine 1-phosphate on Pacemaker Activity in Rabbit Sino-atrial Node Cells", Pflugers Arch, vol. 438, pp. 642-648, (1999).

Hale, J., et al., "Selecting Against $S1P_3$ Enhances the Acute Cardiovascular Tolerability of 3-(N-benzyl)aminopropylphosphonic Acid S1P Receptor Agonists", Bioorganic & Medicinal Chemistry Letters, vol. 14(13), pp. 3501-3505, (2004).

Himmel, H., et al., "Evidence for Edg-3 Receptor-Mediated Activation of $I_{K,Ach}$ by Sphingosine-1-Phosphate in Human Atrial Cardiomyocytes", Molecular Pharmacology, vol. 58, pp. 449-454, (2000).

Huwiler, A., et al., "New Players on the Center Stage: Sphingosine 1-Phosphate and its Receptors as Drug Targets", Biochemical Pharmacology, Pergamon Press, Oxford, GB, vol. 75, pp. 1893-1900, (2008).

Kappos, L., et al., "Oral Fingolimod (FTY720) for Relapsing Multiple Sclerosis", The New England Journal of Medicine, vol. 355(11), pp. 1124-1140, (2006).

Kovarik, J.M., et al., "A Mechanistic Study to Assess Whether Isoproterenol Can Reverse the Negative Chronotropic Effect of Fingolimod", Journal of Clinical Pharmacology, vol. 48, No. 3, pp. 303-310, (2008).

Koyrakh, L., et al., "The Heart Rate Decrease Caused by Acute FTY720 Administration is Mediated by the G Protein-Gated Potassium Channel $I_{KACh}$", American Journal of Transplantation, vol. 5, pp. 529-536, (2005).

Martinet, et al., Journal of the National Cancer Institute, (2000), National Cancer Institute, vol. 92, No. 11, pp. 931-936.

Ochi, R., et al., "Sphingosine-1-Phosphate Effects on Guinea Pig Atrial Myocytes: Alterations in Action Potentials and $K^+$Currents", Cardiovascular Research, vol. 70, pp. 88-96, (2006).

Peters, S., et al., "Sphingosine-1-Phosphate Signaling in the Cardiovascular System", Current Opinion in Pharmacology, vol. 7(2), pp. 186-192, (2007).

Remington, The Science and Practice of Pharmacy, $21^{st}$ Edition (2005), Part 5, "Pharmaceutical Manufacturing" [published by Lippincott Williams & Wilkins].

Sanna, M.G., et al., "Sphingosine 1-Phosphate (S1P) Receptor Subtypes $S1P_1$ and $S1P_3$, Respectively, Regulate Lymphocyte Recirculation and Heart Rate", The Journal of Biological Chemistry, vol. 279(14), pp. 13839-13848, (2004).

Smith, et al., Annals of Neurology, (2003), American Neurological Association, vol. 54, pp. 186-196.

Surh, Nature Reviews Cancer, 2003, Nature Publishing Group, vol. 3, pp. 768-780.

* cited by examiner

PROCESS FOR THE PREPARATION OF 2-IMINO-THIAZOLIDIN-4-ONE DERIVATIVES

CROSS REFERENCE TO RELATED APPLICATIONS

This application is a U.S. filing under 35 USC 371 of PCT/IB2007/054752 filed on Nov. 22, 2007, which claims the benefit of PCT/IB2006/054409 filed on Nov. 23, 2006.

FIELD OF THE INVENTION

The present invention relates to a new process for the preparation of 2-imino-thiazolidin-4-one compounds of the Formula (I) and (II) and to compounds of Formula (II) as such. The present compounds of Formula (II) can be used as intermediates in the preparation of thiazolidin-4-one derivatives of the General Formula (II), said derivatives being described in the PCT Patent Application with the publication number WO 2005/054215. These compounds of General Formula (II) are described in WO 2005/054215 to act as immunosuppressive agents.

DESCRIPTION OF THE INVENTION

In a first aspect the present invention relates to a new process for the preparation of a compound of the Formula (I):

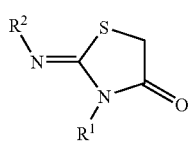

Formula (I)

wherein
$R^1$ represents phenyl which is optionally mono-, di- or tri-substituted wherein the substituents are independently selected from $C_{1-7}$-alkyl and halogen; and
$R^2$ represents $C_{1-7}$-alkyl;
which process comprises reacting a compound of the formula $R^1$—N=C=S, wherein $R^1$ is as defined for Formula (I), with a compound of the formula $R^2$—$NH_2$, wherein $R^2$ is as defined for Formula (I), followed by reaction with bromo-acetyl bromide and a pyridine base.

Preferably the above process is performed without the isolation and/or purification of intermediates such as the thio-urea intermediate that occurs after reacting a compound of Structure 1 with a compound of Structure 2.

Preferably the pyridine base that is used in the preparation processes described herein is pyridine, lutidine or a cholidine, preferably pyridine.

Preferably the above process is used to prepare compounds of Formula (I), wherein $R^1$ represents phenyl which is optionally mono-substituted with $C_{1-7}$-alkyl (such as especially methyl) or halogen, and $R^2$ represents $C_{1-7}$-alkyl (such as especially propyl, isopropyl or butyl).

More preferably the above process is used to prepare compounds of Formula (I), wherein $R^1$ represents phenyl which is optionally mono-substituted with methyl or chloro, and $R^2$ represents propyl, isopropyl or butyl.

Especially preferred, the above process is used to prepare compounds of Formula (I) selected from the group consisting of:
2-[(Z)-isopropylimino]-3-phenyl-thiazolidin-4-one,
3-phenyl-2-[(Z)-propylimino]-thiazolidin-4-one,
2-[(Z)-n-butylimino]-3-phenyl-thiazolidin-4-one,
2-[(Z)-isopropylimino]-3-o-tolyl-thiazolidin-4-one,
2-[(Z)-isopropylimino]-3-(3-chlorophenyl)-thiazolidin-4-one, and
2-[(Z)-propyl imino]-3-o-tolyl-thiazolidin-4-one.

In a further aspect the present invention relates to a process for the preparation of a compound of Formula (II):

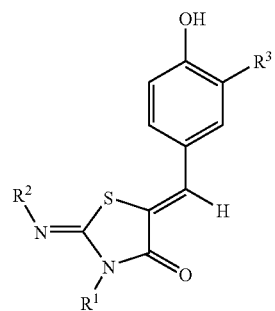

Formula (II)

wherein
$R^1$ and $R^2$ are as defined for Formula (I) above; and
$R^3$ represents hydrogen, hydroxy, $C_{1-7}$-alkoxy, or halogen;
which process comprises preparing a compound of Formula (I) according to the procedure described above and reacting such compound of Formula (I) with a compound of Structure 3:

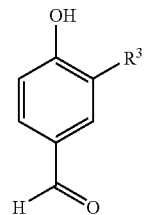

Structure 3 wherein $R^3$ is as defined for Formula (II) above.

In a preferred embodiment the present invention relates to a process for the preparation of a compound of Formula (II) as described above, wherein the compound of Formula (I) is reacted with the compound of Structure 3 in the presence of acetic acid and a base (especially sodium acetate), preferably at elevated temperatures, especially at temperatures between 40 and 80° C., preferably at 55° C. The reaction can also be carried out in a non-polar solvent such as toluene or benzene in the presence of an amine such as pyrrolidine or piperidine.

In another aspect the present invention relates to a process for the preparation of a compound of the Formula (II), wherein $R^1$, $R^2$ and $R^3$ are as defined above, which process comprises reacting a compound of the formula $R^1$—N=C=S, wherein $R^1$ is as defined for Formula (I), with a compound of the formula $R^2$—$NH_2$, wherein $R^2$ is as defined for Formula (I), followed by reaction with bromo-acetyl bromide and a pyridine base, such as especially pyridine, to obtain a compound of Formula (I) (especially wherein the preparation of the compound of Formula (I) occurs without the isolation and/or purification of intermediates), followed by reaction with a compound of Structure 3, wherein $R^3$ is as defined above, characterized in that the compound of Formula (I) is not isolated and/or purified, i.e. for example without any extractive aqueous work-up and concentration to dryness.

In a preferred embodiment the present invention relates to a process for the preparation of a compound of Formula (II) as described in the preceding paragraph, wherein the preparation of the compound of Formula (I) occurs in the presence of dichloromethane, followed by a solvent change in order that the reaction with a compound of Structure 3 occurs in the solvent acetic acid and in the presence of a base (especially sodium acetate), preferably at elevated temperatures, especially at temperatures between 40 and 80° C., preferably at 55° C. The reaction with a compound of Structure 3 can also be carried out in a non-polar solvent such as toluene or benzene in the presence of an amine such as pyrrolidine or piperidine.

Preferably the above processes are used to prepare compounds of Formula (II), wherein $R^1$ represents phenyl which is optionally mono-substituted with $C_{1-7}$alkyl (such as especially methyl) or halogen, $R^2$ represents $C_{1-7}$-alkyl (such as especially propyl, isopropyl or butyl), and $R^3$ represents hydrogen, $C_{1-7}$-alkoxy (such as especially methoxy), or halogen.

More preferably the above processes are used to prepare compounds of Formula (II), wherein $R^1$ represents phenyl which is optionally mono-substituted with methyl or chloro, $R^2$ represents propyl, isopropyl or butyl, and $R^3$ represents hydrogen, methoxy, or chloro.

Especially preferred, the above processes are used to prepare compounds of Formula (II) selected from the group consisting of:
5-(3-chloro-4-hydroxy-benz-(Z)-ylidene)-2-[(Z)-isopropylimino]-3-phenyl-thiazolidin-4-one,
5-(3-chloro-4-hydroxy-benz-(Z)-ylidene)-2-[(Z)-propylimino]-3-phenyl-thiazolidin-4-one,
5-(3-chloro-4-hydroxy-benz-(Z)-ylidene)-2-[(Z)-butylimino]-3-phenyl-thiazolidin-4-one,
5-(3-chloro-4-hydroxy-benz-(Z)-ylidene)-2-[(Z)-isopropylimino]-3-(o-tolyl)-thiazolidin-4-one,
5-(3-chloro-4-hydroxy-benz-(Z)-ylidene)-2-[(Z)-isopropyl imino]-3-(3-chloro-phenyl)-thiazolidin-4-one,
5-(3-chloro-4-hydroxy-benz-(Z)-ylidene)-2-[(Z)-propylimino]-3-(o-tolyl)-thiazolidin-4-one,
5-(4-hydroxy-benz-(Z)-ylidene)-2-[(Z)-propylimino]-3-phenyl-thiazolidin-4-one,
5-(4-hydroxy-3-methoxy-benz-(Z)-ylidene)-2-[(Z)-propyl imino]-3-phenyl-thiazolidin-4-one,
5-(4-hydroxy-benz-(Z)-ylidene)-2-[(Z)-butylimino]-3-phenyl-thiazolidin-4-one,
5-(4-hydroxy-3-methoxy-benz-(Z)-ylidene)-2-[(Z)-butylimino]-3-phenyl-thiazolidin-4-one,
5-(4-hydroxy-benz-(Z)-ylidene)-2-[(Z)-propylimino]-3-(o-tolyl)-thiazolidin-4-one, and
5-(4-hydroxy-3-methoxy-benz-(Z)-ylidene)-2-[(Z)-propylimino]-3-(3-chlorophenyl)-thiazolidin-4-one.

Also especially preferred, the above processes are used to prepare compounds of Formula (II) selected from the group consisting of:
5-(3-chloro-4-hydroxy-benz-(Z)-ylidene)-2-[(Z)-isopropylimino]-3-Phenyl-thiazolidin-4-one,
5-(4-hydroxy-benz-(Z)-ylidene)-2-[(Z)-propylimino]-3-phenyl-thiazolidin-4-one,
5-(3-chloro-4-hydroxy-benz-(Z)-ylidene)-2-[(Z)-propyl imino]-3-phenyl-thiazolidin-4-one,
5-(4-hydroxy-3-methoxy-benz-(Z)-ylidene)-2-[(Z)-propylimino]-3-phenyl-thiazolidin-4-one,
5-(4-hydroxy-benz-(Z)-ylidene)-2-[(Z)-butylimino]-3-phenyl-thiazolidin-4-one,
5-(3-chloro-4-hydroxy-benz-(Z)-ylidene)-2-[(Z)-butylimino]-3-phenyl-thiazolidin-4-one,
5-(4-hydroxy-3-methoxy-benz-(Z)-ylidene)-2-[(Z)-butylimino]-3-phenyl-thiazolidin-4-one,
5-(3-chloro-4-hydroxy-benz-(Z)-ylidene)-2-[(Z)-isopropylimino]-3-(o-tolyl)-thiazolidin-4-one,
5-(4-hydroxy-benz-(Z)-ylidene)-2-[(Z)-propylimino]-3-(o-tolyl)-thiazolidin-4-one,
5-(3-chloro-4-hydroxy-benz-(Z)-ylidene)-2-[(Z)-propylimino]-3-(o-tolyl)-thiazolidin-4-one, and
5-(4-hydroxy-3-methoxy-benz-(Z)-ylidene)-2-[(Z)-propyl imino]-3-(3-chlorophenyl)-thiazolidin-4-one.

In a further aspect the present invention relates to a compound of the Formula (II), wherein
$R^1$ represents phenyl which is optionally mono-, di- or tri-substituted wherein the substituents are independently selected from $C_{1-7}$-alkyl and halogen;
$R^2$ represents $C_{1-7}$-alkyl; and
$R^3$ represents hydrogen, hydroxy, $C_{1-7}$-alkoxy, or halogen.

In a preferred embodiment, the present invention relates to a compound of the Formula (II), wherein
$R^1$ represents phenyl which is optionally mono-substituted with $C_{1-7}$-alkyl (such as especially methyl) or halogen;
$R^2$ represents $C_{1-7}$-alkyl (such as especially propyl, isopropyl or butyl); and
$R^3$ represents hydrogen, $C_{1-7}$-alkoxy (such as especially methoxy), or halogen.

In an especially preferred embodiment, the present invention relates to a compound of the Formula (II), wherein $R^1$ represents phenyl which is optionally mono-substituted with methyl or chloro, $R^2$ represents propyl, isopropyl or butyl, and $R^3$ represents hydrogen, methoxy, or chloro.

In a more specific embodiment, the present invention relates to a compound of Formula (II) selected from the group consisting of:
5-(3-chloro-4-hydroxy-benz-(Z)-ylidene)-2-[(Z)-isopropylimino]-3-phenyl-thiazolidin-4-one,
5-(3-chloro-4-hydroxy-benz-(Z)-ylidene)-2-[(Z)-propylimino]-3-phenyl-thiazolidin-4-one,
5-(3-chloro-4-hydroxy-benz-(Z)-ylidene)-2-[(Z)-butyl imino]-3-phenyl-thiazolidin-4-one,
5-(3-chloro-4-hydroxy-benz-(Z)-ylidene)-2-[(Z)-isopropyl imino]-3-(o-tolyl)-thiazolidin-4-one,
5-(3-chloro-4-hydroxy-benz-(Z)-ylidene)-2-[(Z)-isopropyl imino]-3-(3-chloro-phenyl)-thiazolidin-4-one,
5-(3-chloro-4-hydroxy-benz-(Z)-ylidene)-2-[(Z)-propyl imino]-3-(o-tolyl)-thiazolidin-4-one,
5-(4-hydroxy-benz-(Z)-ylidene)-2-[(Z)-propylimino]-3-phenyl-thiazolidin-4-one,
5-(4-hydroxy-3-methoxy-benz-(Z)-ylidene)-2-[(Z)-propyl imino]-3-phenyl-thiazolidin-4-one,
5-(4-hydroxy-benz-(Z)-ylidene)-2-[(Z)-butylimino]-3-phenyl-thiazolidin-4-one,
5-(4-hydroxy-3-methoxy-benz-(Z)-ylidene)-2-[(Z)-butylimino]-3-phenyl-thiazolidin-4-one,
5-(4-hydroxy-benz-(Z)-ylidene)-2-[(Z)-propylimino]-3-(o-tolyl)-thiazolidin-4-one, and
5-(4-hydroxy-3-methoxy-benz-(Z)-ylidene)-2-[(Z)-propylimino]-3-(3-chlorophenyl)-thiazolidin-4-one.

Compounds of Formula (II) described herein can be transformed into the compounds of General Formula (II) described in the patent application WO 2005/054215 using standard methods for the alkylation of phenols, like reaction in a solvent such as ethanol in the presence of a base such as sodium hydride, cesium carbonate, potassium carbonate or potassium tert-butoxide, with an appropriate alkyl halide, alkyl tosylate or alkyl triflate.

Any reference hereinbefore or hereinafter to a compound of Formula (I), Formula (II) or Structure 3 is to be understood as referring also to salts of such a compound, as appropriate and expedient.

The term $C_{1-7}$alkyl as used herein means saturated, straight or branched chain groups with one to seven carbon atoms. $C_{1-7}$-alkyl as used for $R^2$ is preferably n-propyl, isopropyl or n-butyl.

The term $C_{1-7}$-alkoxy as used herein means an R—O— group, wherein R is $C_{1-7}$-alkyl.

The term halogen as used herein means fluoro, chloro, bromo or iodo, preferably chloro.

According to the invention, the compounds of Formulae (I) and (II) are manufactured by the methods given below. In general, they are prepared according to the general sequence of reactions outlined below in the General Reaction Scheme.

General Reaction Scheme:

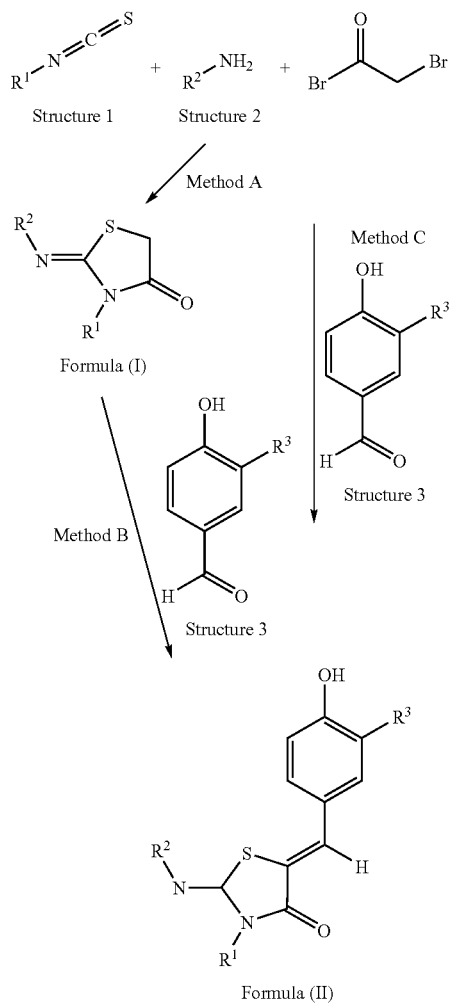

According to the General Reaction Scheme, compounds of the Formula (II) are prepared following Method B by reacting a compound of Formula (I) with a compound of Structure 3, for instance, in a solvent such as acetic acid at elevated temperatures and in the presence of a base such as sodium acetate. The required compounds of Formula (I) are prepared following Method A by reacting an isothiocyanate of Structure 1 successively with an amine of Structure 2, bromo-acetyl bromide and a pyridine base in a solvent such as dichlo-romethane. Alternatively, compounds of Formula (II) can be prepared following Method C without isolating and/or purifying the compounds of Formula (I), such that an isothiocyanate of Structure 1 is reacted successively with an amine of Structure 2, bromo-acetyl bromide and a pyridine base in a solvent such as dichloromethane, followed by the addition of an aldehyde of Structure 3, for instance, in a solvent such as acetic acid at elevated temperatures and in the presence of a base such as sodium acetate. The compounds of Structure 1, 2 and 3 are either commercially available or can be prepared according to procedures known to a person skilled in the art.

EXAMPLES

The following examples illustrate the invention.

All temperatures given are external temperatures and are stated in °C. Compounds are characterized by $^1$H-NMR (400 MHz) or $^{13}$C-NMR (100 MHz) (Bruker; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm 120 Å, gradient: 5-95% acetonitrile in water, 1 min, with 0.04% trifluoroacetic acid, flow: 4.5 mL/min), $t_R$ is given in minutes. Melting point is measured on Büchi melting point apparatus B540 and is not corrected.

ABBREVIATIONS

DMSO dimethylsulfoxide
h hour(s)
LC-MS liquid chromatography—mass spectrometry
min minute(s)
m.p. melting point
$t_R$ retention time Typical Procedure for the Preparation of the 2-imino-thiazolidin-4-ones of Formula (I) (Method A)

To a solution of an arylisothiocyanate of Structure 1 (14.8 mmol) in dichloromethane (20 mL) is added portionwise an alkyl amine of Structure 2 (14.8 mmol) at 20° C. The solution is stirred at 20° C. for 15 min. The solution is cooled to 0° C. Bromo-acetyl bromide (1.287 mL, 14.8 mmol) is added carefully such that the temperature does not rise above 5° C. The reaction mixture is stirred at 0° C. for 15 min. To the reaction mixture is added pyridine (2.453 mL, 30.3 mmol) at 0° C. The mixture is stirred for another 15 min. The mixture is warmed to 20° C. The reaction mixture is washed with water (10 mL). The aqueous layer is extracted with dichloromethane (10 mL). The organic layers are combined and evaporated under reduced pressure to afford a 2-imino-thiazolidin-4-one of Formula (I).

Scaffold 1:

2-[(Z)-Isopropylimino]-3-phenyl-thiazolidin-4-one is prepared as described in Method A. LC-MS: $t_R$=0.58 min, [M+1]$^+$=235; $^1$H-NMR (CDCl$_3$): δ 7.51-7.47 (m, 2H), 7.43-

7.35 (m, 1H), 7.31-7.29 (m, 2H), 3.99 (s, 2H), 3.53 (hept, J=6.2 Hz, 1H), 1.15 (d, J=6.2 Hz, 6H); $^{13}$C-NMR (CDCl$_3$): δ 171.3, 135.2, 129.0, 128.5, 128.0, 125.8, 53.8, 32.6, 23.2.

Scaffold 2:

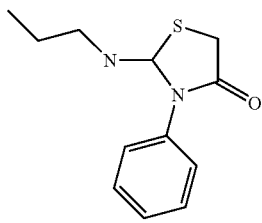

(I)b

3-Phenyl-2-[(Z)-propylimino]-thiazolidin-4-one is prepared as described in Method A. LC-MS: $t_R$=0.60 min, [M+1]$^+$=235; $^1$H-NMR (CDCl$_3$): δ 7.51-7.36 (m, 3H), 7.28-7.24 (m, 2H), 3.99 (s, 2H), 3.27 (t, J=7.0 Hz, 2H), 1.60 (hex, J=7.0 Hz, 2H), 0.91 (t, J=7.6 Hz, 3H); $^{13}$C-NMR (CDCl$_3$): δ 171.3, 135.1, 129.2, 128.7, 128.0, 121.0, 54.2, 32.7, 23.5, 11.8.

Scaffold 3:

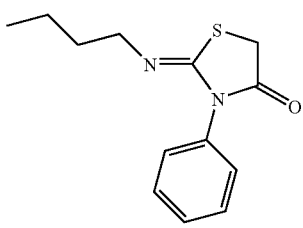

(I)c

2-[(Z)-n-Butylimino]-3-phenyl-thiazolidin-4-one is prepared as described in Method A. LC-MS: $t_R$=0.69 min, [M+1]$^+$=249; $^1$H-NMR (CDCl$_3$): δ 7.52-7.48 (m, 2H), 7.44-7.40 (m, 1H), 7.30-7.28 (m, 2H), 4.00 (s, 2H), 3.32 (t, J=7.0 Hz, 2H), 1.58 (p, 2H), 1.35 (sex, J$_1$=7.2, 2H), 0.93 (t, J=7.4 Hz, 3H); $^{13}$C-NMR (CDCl$_3$): δ 171.3, 135.1, 129.2, 128.7, 128.0, 121.0, 52.2, 32.7, 32.3, 20.5, 13.9.

Scaffold 4:

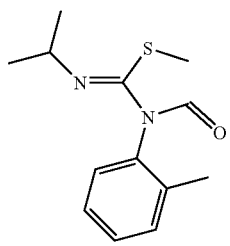

(I)d

2-[(Z)-Isopropylimino]-3-o-tolyl-thiazolidin-4-one is obtained following Method A. LC-MS: $t_R$=0.67 min, [M+1]$^+$=249; $^1$H-NMR (CDCl$_3$): δ 7.35-7.28 (m, 3H), 7.15-7.13 (m, 1H), 4.00 (s, 2H), 3.51 (hept, J=6.4 Hz, 1H), 2.18 (s, 3H), 1.12 (d, 3H), 1.11 (d, 3H); $^{13}$C-NMR (CDCl$_3$): δ 171.1, 136.1, 134.6, 131.1, 129.2, 128.6, 126.9, 53.9, 32.6, 23.4, 23.3, 17.6.

Scaffold 5:

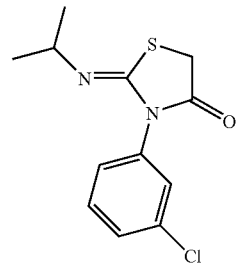

(I)e

2-[(Z)-Isopropylimino]-3-(3-chlorophenyl)-thiazolidin-4-one is prepared as described in Method A. LC-MS: $t_R$=0.76 min, [M+1]$^+$=269; $^1$H-NMR (CDCl$_3$): δ 7.43-7.20 (m, 4H), 3.98 (s, 2H), 3.51 (hept, J=6.2 Hz, 1H), 1.15 (d, 6H); $^{13}$C-NMR (CDCl$_3$): δ 171.0, 136.2, 134.4, 129.9, 128.7, 128.5, 126.4, 53.9, 32.5, 23.3.

Scaffold 6:

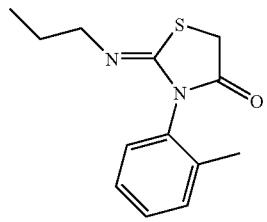

(I)f

2-[(Z)-Propylimino]-3-o-tolyl-thiazolidin-4-one is obtained following Method A.

LC-MS: $t_R$=0.67 min, [M+1]$^+$=249; $^1$H-NMR (CDCl$_3$): δ 7.34-7.26 (m, 3H), 7.14-7.09 (m, 1H), 4.02 (s, 2H), 3.34-3.22 (m, 2H), 2.20 (s, 3H), 1.63-1.54 (m, 2H), 0.90 (t, J=7.4 Hz, 3H); $^{13}$C-NMR (CDCl$_3$): δ 171.1, 136.1, 134.5, 131.1, 129.4, 128.6, 127.1, 54.4, 32.6, 23.6, 17.6, 11.8.

TABLE 1

Summary of the results of the synthesis of the 2-imino-thiazolidin-4-ones of Formula (I)

| Scaffold | Compound | Yield [%] | Ratio of isomers[a] | Purity of compound of Formula (I) by LC-MS [area %][b] |
|---|---|---|---|---|
| 1 | (I)a | 79 | 95.0:5.0 | 78.5 |
| 2 | (I)b | 53 | 91.5:8.5 | 85.4 |
| 3 | (I)c | 74 | 93.0:7.0 | 89.0 |
| 4 | (I)d | 73 | 97.0:3.0 | 93.6 |
| 5 | (I)e | 77 | 96.6:3.4 | 90.1 |
| 6 | (I)f | 72 | 95.5:4.5 | 85.4 |

[a] Determined by $^1$H-NMR
[b] at 230 nm

The ratio of isomers as given in the above Table 1 refers to the ratio of the major regioisomer of Formula (I) to the minor regioisomer of Formula (III) as determined by $^1$H-NMR.

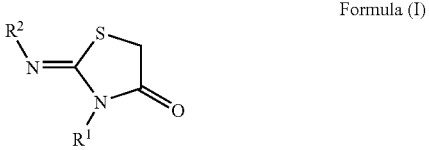

Formula (I)

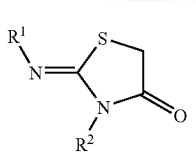

Formula (III)

Typical Procedure for the Knoevenagel Condensation of Compounds of Formula (I) with Compounds of Structure 3 to Give Compounds of Formula (II) (Method B)

A solution of a 2-imino-thiazolidin-4-one of Formula (I) (4.27 mmol), a 4-hydroxy-benzaldehyde of Structure 3 (4.27 mmol) and sodium acetate (700 mg, 8.54 mmol) in acetic acid (10 mL) is stirred at 60° C. for 15 h. The suspension is cooled to 20° C. and filtered. The cake on the nutsche is washed with a mixture of water and acetic acid (5 mL, 1/1 [v]/[v]). The product is dried under reduced pressure.

Example 1

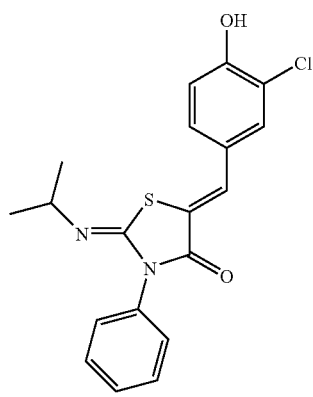

(II)a 5-(3-Chloro-4-hydroxy-benz-(Z)-ylidene)-2-[(Z)-isopropylimino]-3-phenyl-thiazolidin-4-one is obtained following Method B.

LC-MS: $t_R$=1.02 min, [M+1]$^+$=373;

$^1$H-NMR (deutero DMSO): δ 10.9 (s br, 1H), 7.68-7.65 (m, 2H), 7.52-7.49 (m, 3H), 7.45-7.35 (m, 3H), 7.15 (d, J=8.5 Hz, 1H), 3.55 (hept, J=6.2 Hz, 1H), 1.10 (d, J=6.2 Hz, 6H);

$^{13}$C-NMR (deutero DMSO): δ 166.0, 155.2, 146.1, 135.9, 132.4, 130.4, 129.3, 128.9, 128.8, 126.3, 121.0, 119.1, 117.7, 54.8, 24.0;

m.p.: 270° C.

Example 2

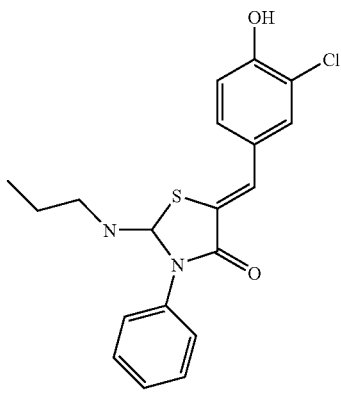

(II)b 5-(3-Chloro-4-hydroxy-benz-(Z)-ylidene)-2-[(Z)-propylimino]-3-phenyl-thiazolidin-4-one is obtained following Method B.

LC-MS: $t_R$=1.01 min, [M+1]$^+$=373;

$^1$H-NMR (deutero DMSO): 610.2 (s br, 1H), 7.66 (s, 1H), 7.55-7.48 (m, 4H), 7.45-7.41 (m, 1H), 7.37-7.35 (m, 2H), 6.95 (d, J=8.3 Hz, 2H), 3.29 (t, J=6.8 Hz, 2H), 1.54 (hex, J=7.3, 2H), 0.86 (t, J=7.3 Hz, 3H);

$^{13}$C-NMR (deutero DMSO): δ 166.1, 155.2, 147.8, 135.9, 132.4, 130.3, 129.3, 128.9, 128.8, 126.3, 121.0, 119.2, 117.7, 54.7, 23.8, 12.2;

m.p.: 200° C.

Example 3

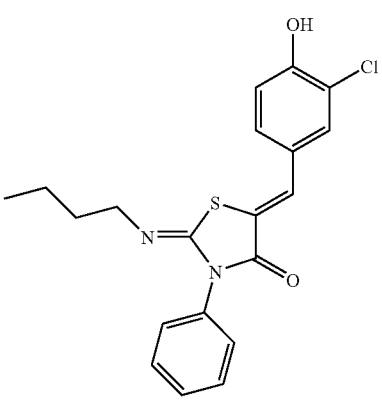

(II)c 5-(3-Chloro-4-hydroxy-benz-(Z)-ylidene)-2-[(Z)-butyl imino]-3-phenyl-thiazolidin-4-one is obtained following Method B.

LC-MS: $t_R$=1.05 min, [M+1]$^+$=387;

$^1$H-NMR (deutero DMSO): δ 11.0 (s br, 1H), 7.69-7.66 (m, 2H), 7.52-7.48 (m, 3H), 7.45-7.41 (m, 1H), 7.37-7.35 (m, 2H), 7.15 (d, J=8.5 Hz, 1H), 3.33 (t, J=6.8 Hz, 2H), 1.54-1.46 (m, 2H), 1.34-1.25 (m, 2H), 0.87 (t, J=7.3 Hz, 3H);

$^{13}$C-NMR (deutero DMSO): δ 166.0, 155.4, 147.7, 135.9, 132.5, 130.3, 129.4, 128.95, 128.86, 128.2, 126.2, 121.0, 119.1, 117.7, 52.7, 32.7, 20.4, 14.2;

m.p.: 192° C.

Example 4

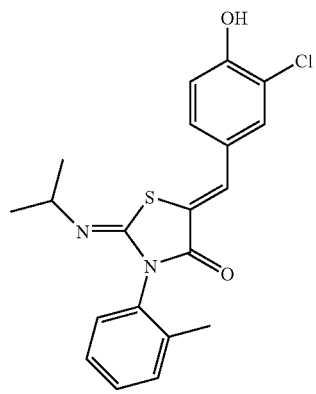

(II)d 5-(3-Chloro-4-hydroxy-benz-(Z)-ylidene)-2-[(Z)-isopropylimino]-3-(o-tolyl)-thiazolidin-4-one is obtained following Method B.

LC-MS: $t_R$=1.04 min, [M+1]$^+$=387;
$^1$H-NMR (deutero DMSO): δ 11.0 (s br, 1H), 7.70-7.66 (m, 2H), 7.53-7.51 (m, 1H), 7.38-7.25 (m, 4H), 7.15 (d, J=8.3 Hz, 1H), 3.55 (hept, J=6.0 Hz, 1H), 2.08 (s, 3H), 1.10 (d, J=5.9 Hz, 3H), 1.08 (d, 3H);
$^{13}$C-NMR (deutero DMSO): δ 165.8, 155.3, 145.3, 136.3, 135.2, 132.5, 131.1, 130.4, 129.50, 129.46, 129.0, 127.3, 126.2, 121.1, 119.0, 117.7, 54.9, 24.1, 24.0, 17.6;
m.p.: 252° C.

Example 5

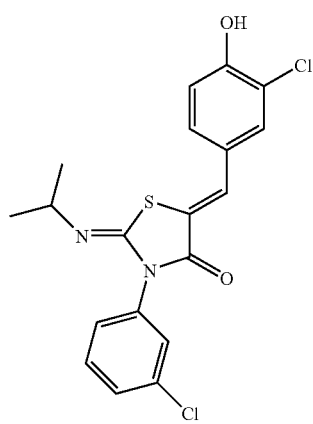

(II)e 5-(3-Chloro-4-hydroxy-benz-(Z)-ylidene)-2-[(Z)-isopropylimino]-3-(3-chloro-phenyl)-thiazolidin-4-one is obtained following Method B.
LC-MS: $t_R$=1.07 min, [M+1]$^+$=407;
$^1$H-NMR (deutero DMSO): δ 11.0 (s br, 1H), 7.68-7.67 (m, 2H), 7.56-7.49 (m, 4H), 7.39-7.37 (m, 1H), 7.15 (d, J=8.3 Hz, 1H), 3.55 (hept, J=6.0 Hz, 1H), 1.10 (d, J=6.5 Hz, 3H);
$^{13}$C-NMR (deutero DMSO): δ 165.9, 155.5, 145.9, 137.2, 133.3, 132.5, 130.9, 130.4, 129.05, 129.01, 128.9, 127.9, 126.1, 121.1, 118.8, 117.8, 54.8, 24.0;
m.p.: 272° C.

Example 6

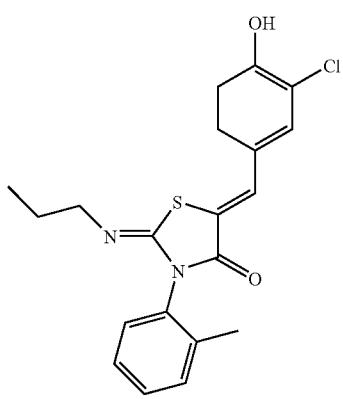

(II)f 5-(3-Chloro-4-hydroxy-benz-(Z)-ylidene)-2-[(Z)-propylimino]-3-(o-tolyl)-thiazolidin-4-one is obtained following Method B.

LC-MS: $t_R$=1.03 min, [M+1]$^4$=387;
$^1$H-NMR (deutero DMSO): δ 11.0 (s br, 1H), 7.70-7.67 (m, 2H), 7.53-7.51 (m, 1H), 7.38-7.25 (m, 4H), 7.15 (d, J=8.3 Hz, 1H), 3.36-3.24 (m, 2H), 2.09 (s, 3H), 1.56-1.47 (m, 2H), 0.84 (t, J=7.3 Hz, 3H);
$^{13}$C-NMR (deutero DMSO): δ 165.8, 155.3, 147.0, 136.3, 135.2, 132.5, 131.1, 130.3, 129.53, 129.50, 129.0, 127.3, 126.2, 121.1, 119.0, 117.8, 54.8, 23.9, 17.6, 12.2;
m.p.: 199° C.

TABLE 2

Summary of the results of the Knoevenagel reactions yielding compounds of Formula (II), following Method B

| Example | Compound | Yield [%] | Purity of compound of Formula (II) by LC-MS [area %][a] |
|---------|----------|-----------|---------------------------------------------------------|
| 1 | (II)a | 71 | 100 |
| 2 | (II)b | 77 | 100 |
| 3 | (II)c | 84 | 100 |
| 4 | (II)d | 73 | 100 |
| 5 | (II)e | 60 | 100 |
| 6 | (II)f | 69 | 100 |

[a] at 254 nm

Typical One-Pot Procedure for the Preparation of the Knoevenagel Products of Formula (II) (Method C)

To a solution of an arylisothiocyanate of Structure 1 (14.8 mmol) in dichloromethane (20 mL) is added portionwise an alkyl amine of Structure 2 (14.8 mmol) at 20° C. The solution is stirred at 20° C. for 15 min. The solution is cooled to 0° C. Bromo-acetyl bromide (1.287 mL, 14.8 mmol) is added carefully such that the temperature does not rise above 5° C. The reaction mixture is stirred at 0° C. for 15 min. To the reaction mixture is added pyridine (2.453 mL, 30.3 mmol) at 0° C. The mixture is stirred for another 15 min. The mixture is warmed to 20° C. An in-process control is performed to determine the ratio of the regioisomers of Formula (I) and (III). Dichloromethane is removed under reduced pressure. To the residue is added a 4-hydroxy-benzaldehyde of Structure 3 (14.8 mmol), sodium acetate (2.427 g, 29.6 mmol) and acetic acid (20 mL). The reaction mixture is stirred at 60° C. for 15 h. The suspension is cooled to 20° C. and water (20 mL) is added. The suspension is filtered. The cake on the nutsche is washed with a mixture of water and acetic acid (10 mL, 1/1 [v]/[v]). The product is dried under reduced pressure.

In an alternative Method C', the same procedure is followed as described for Method C above, except for the following variations: The major part of dichloromethane is removed at ambient pressure at elevated temperatures (55-65° C.). Instead of cooling the suspension to 20° C. and adding water after the reaction with the benzaldehyde of Structure 3, more solvent is removed under reduced pressure and 75-85° C., and water (20 mL) is added at 60° C. The suspension is then filtered and the cake on the nutsche is washed with a mixture of water and acetic acid (10 mL), optionally followed by a wash with water (10 mL). The product is then dried under reduced pressure at 20-75° C.

Example 7

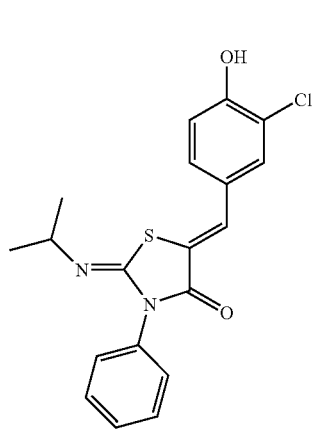

(II)a 5-(3-Chloro-4-hydroxy-benz-(Z)-ylidene)-2-[(Z)-isopropylimino]-3-phenyl-thiazolidin-4-one is obtained following Method C.

For analytical data see Example 1.

Example 8

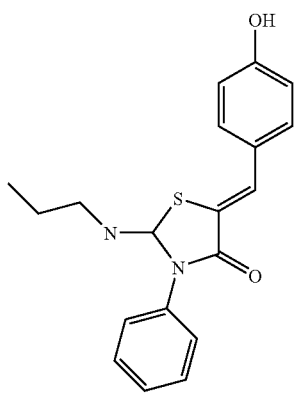

(II)g 5-(4-Hydroxy-benz-(Z)-ylidene)-2-[(Z)-propylimino]-3-phenyl-thiazolidin-4-one is obtained following Method C.

LC-MS: $t_R$=0.93 min, [M+1]$^+$=339;

$^1$H-NMR (deutero DMSO): δ 10.2 (s br, 1H), 7.66 (s, 1H), 7.55-7.48 (m, 4H), 7.45-7.41 (m, 1H), 7.37-7.35 (m, 2H), 6.95 (d, J=8.3 Hz, 2H), 3.29 (t, J=6.8 Hz, 2H), 1.54 (hex, J=7.3, 2H), 0.86 (t, J=7.3 Hz, 3H);

$^{13}$C-NMR (deutero DMSO): δ 166.3, 159.9, 148.2, 136.0, 132.6, 130.3, 129.3, 129.0, 128.8, 125.0, 117.3, 116.8, 54.6, 23.8, 12.2;

m.p.: 232° C.

Example 9

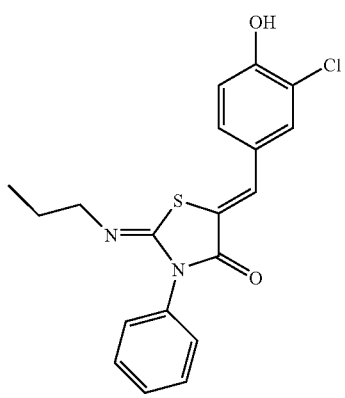

(II)b 5-(3-Chloro-4-hydroxy-benz-(Z)-ylidene)-2-[(Z)-propylimino]-3-phenyl-thiazolidin-4-one is obtained following Method C.

For analytical data see Example 2.

Example 10

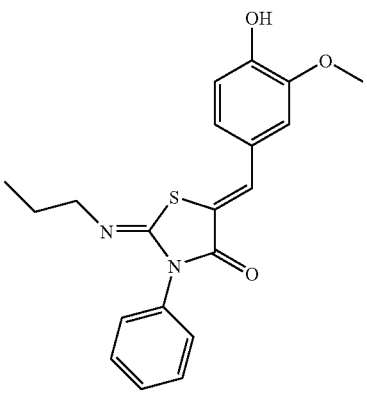

(II)h 5-(4-Hydroxy-3-methoxy-benz-(Z)-ylidene)-2-[(Z)-propylimino]-3-phenyl-thiazolidin-4-one is obtained following Method C.

LC-MS: $t_R$=0.95 min, [M+1]$^+$=369;

$^1$H-NMR (deutero DMSO): δ 9.84 (s br, 1H), 7.69 (s, 1H), 7.53-7.49 (m, 2H), 7.45-7.42 (m, 1H), 7.38-7.36 (m, 2H), 7.26 (s, 1H), 7.16 (d, J=7.8 Hz, 1H), 6.97 (d, J=8.3 Hz, 1H), 3.84 (s, 3 H), 3.30 (t, J=6.8 Hz, 2H), 1.54 (hex, J=7.3 Hz, 2H), 0.86 (t, J=7.3 Hz, 3H);

$^{13}$C-NMR (deutero DMSO): δ 166.2, 149.4, 148.4, 135.9, 130.7, 129.4, 129.0, 128.8, 125.4, 123.9, 121.0, 117.5, 116.7, 115.1, 56.2, 54.5, 23.8, 12.2;

m.p.: 173° C.

Example 11

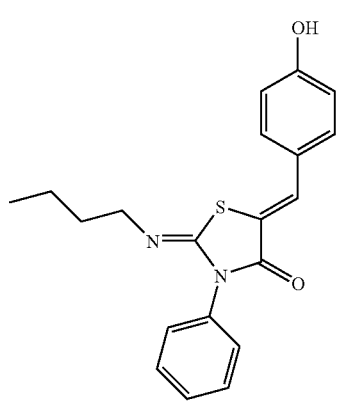

(II)i 5-(4-Hydroxy-benz-(Z)-ylidene)-2-[(Z)-butylimino]-3-phenyl-thiazolidin-4-one is obtained following Method C.

LC-MS: $t_R$=0.98 min, $[M+1]^+$=353;

$^1$H-NMR (deutero DMSO): δ 10.2 (s br, 1H), 7.67 (s, 1H), 7.55-7.48 (m, 4H), 7.44-7.41 (m, 1H), 7.37-7.35 (m, 2H), 6.95 (d, J=8.3 Hz, 2H), 3.33 (t, J=6.8 Hz, 2H), 1.54-1.47 (m, 2H), 1.34-1.25 (m, 2H), 0.87 (t, J=7.3 Hz, 3H);

$^{13}$C-NMR (deutero DMSO): δ 166.3, 159.9, 148.1, 136.0, 132.6, 130.3, 129.3, 129.0, 128.8, 125.0, 117.3, 116.7, 52.7, 32.7, 20.4, 14.2;

m.p.: 228° C.

Example 13

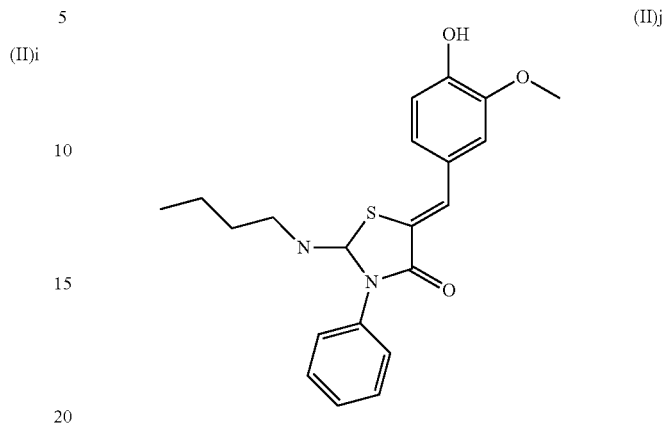

(II)j 5-(4-Hydroxy-3-methoxy-benz-(Z)-ylidene)-2-[(Z)-butylimino]-3-phenyl-thiazolidin-4-one is obtained following Method C.

LC-MS: $t_R$=0.99 min, $[M+1]^+$=383;

$^1$H-NMR (deutero DMSO): δ 9.86 (s br, 1H), 7.68 (s, 1H), 7.52-7.49 (m, 2H), 7.45-7.41 (m, 1H), 7.37-7.35 (m, 2H), 7.26 (s, 1H), 7.15 (d, J=8.3 Hz, 1H), 6.97 (d, J=8.3 Hz, 1H), 3.84 (s, 3H), 3.34 (t, J=6.8 Hz, 2H), 1.54-1.46 (m, 2H), 1.34-1.25 (m, 2H), 0.87 (t, J=7.3 Hz, 3H);

$^{13}$C-NMR (deutero DMSO): δ 166.2, 149.4, 148.4, 148.1, 136.0, 130.6, 129.3, 129.0, 128.8, 125.5, 123.9, 117.5, 116.7, 115.1, 56.2, 52.6, 32.6, 20.3, 14.2;

m.p.: 164° C.

Example 12

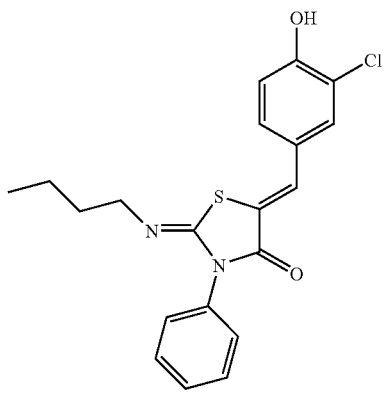

(II)c 5-(3-Chloro-4-hydroxy-benz-(Z)-ylidene)-2-[(Z)-butylimino]-3-Phenyl-thiazolidin-4-one is obtained following Method C.

For analytical data see Example 3.

Example 14

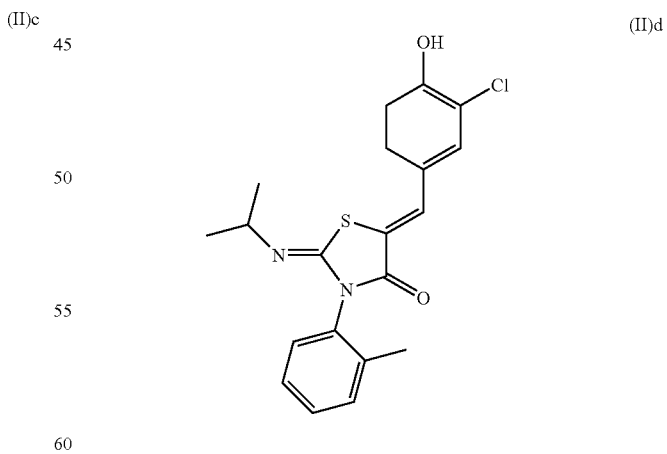

(II)d 5-(3-Chloro-4-hydroxy-benz-(Z)-ylidene)-2-[(Z)-isopropylimino]-3-(o-tolyl)-thiazolidin-4-one is obtained following Method C.

For analytical data see Example 4.

Example 15

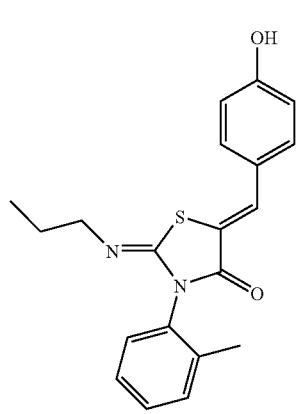

(II)k 5-(4-Hydroxy-benz-(Z)-ylidene)-2-[(Z)-propylimino]-3-(o-tolyl)-thiazolidin-4-one is obtained following Method C.

LC-MS: $t_R$=0.97 min, [M+1]$^+$=353;

$^1$H-NMR (deutero DMSO): δ 11.1 (s br, 1H), 7.67 (s, 1H), 7.55-7.54 (m, 2H), 7.38-7.24 (m, 4H), 6.95 (d, J=8.3 Hz, 2H), 3.36-3.24 (m, 2H), 2.09 (s, 3H), 1.56-1.47 (m, 2H), 0.84 (t, J=7.3 Hz, 3H);

$^{13}$C-NMR (deutero DMSO): δ 166.0, 159.9, 147.5, 136.3, 135.3, 132.7, 131.1, 130.4, 129.6, 129.4, 127.3, 124.9, 117.2, 116.8, 54.7, 23.9, 17.6, 12.2;

m.p.: 198° C.

Example 16

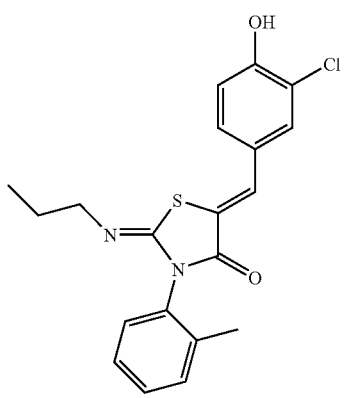

(II)f 5-(3-Chloro-4-hydroxy-benz-(Z)-ylidene)-2-[(Z)-propylimino]-3-(o-tolyl)-thiazolidin-4-one is obtained following Method C.

For analytical data see Example 6.

Example 17

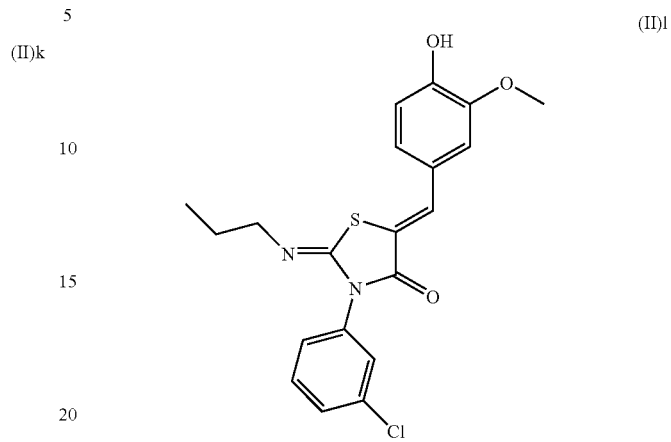

(II)l 5-(4-Hydroxy-3-methoxy-benz-(Z)-ylidene)-2-[(Z)-propylimino]-3-(3-chlorophenyl)-thiazolidin-4-one is obtained following Method C.

LC-MS: $t_R$=1.02 min, [M+1]$^+$=403;

$^1$H-NMR (deutero DMSO): δ 9.86 (s br, 1H), 7.69 (s, 1H), 7.56-7.50 (m, 3H), 7.40-7.37 (m, 1H), 7.26 (s, 1H), 7.16 (d, J=8.5 Hz, 1H), 6.97 (d, J=7.5 Hz, 1H), 3.85 (s, 3H), 3.30 (t, J=6.9 Hz, 2H), 1.59-1.50 (m, 2H), 0.87 (t, J=7.4 Hz, 3H);

$^{13}$C-NMR (deutero DMSO): δ 166.0, 149.5, 148.4, 148.0, 137.2, 133.3, 130.86, 130.80, 129.1, 128.9, 128.0, 125.4, 123.9, 117.5, 116.7, 115.2, 56.2, 54.5, 23.9, 12.2;

m.p.: 200° C.

TABLE 3

Results of the one-pot procedure yielding compounds of Formula (II) following Method C

| Example | Compound | Yield [%] | Ratio of isomers of intermediates of Formula (I) and (III)[a] | Purity of compound of Formula (II) by LC-MS [area %][b] |
| --- | --- | --- | --- | --- |
| 7  | (II)a | 88 | 97:3 | 100 |
| 8  | (II)g | 80 | 94:6 | 100 |
| 9  | (II)b | 80 | 94:6 | 89.0 |
| 10 | (II)h | 96 | 93:7 | 100 |
| 11 | (II)i | 82 | 94:6 | 100 |
| 12 | (II)c | 86 | 94:6 | 97 |
| 13 | (II)j | 84 | 94:6 | 76 |
| 14 | (II)d | 83 | 96:4 | 100 |
| 15 | (II)k | 78 | 97:3 | 94 |
| 16 | (II)f | 84 | 97:3 | 98 |
| 17 | (II)l | 84 | 95:5 | 100 |

[a] Determined by LC-MS at 250 nm after addition of pyridine, prior to the solvent change to acetic acid.
[b] at 254 nm The ratio of isomers as given in the above Table 3 refers to the ratio of the major regioisomer of Formula (I) to the minor regioisomer of Formula (III), said isomers occurring as intermediates in the preparation of compounds of Formula (II). The ratio of the isomers is determined by LC-MS in an in-process control.

The invention claimed is:

1. A compound of the Formula (II):

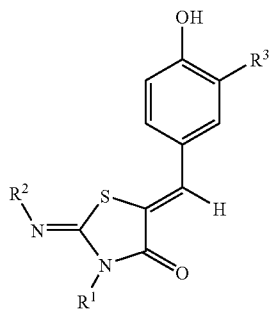

Formula (II)

wherein
- $R^1$ represents phenyl which is optionally mono-, di- or tri-substituted wherein the substituents are independently selected from $C_{1-7}$-alkyl and halogen;
- $R^2$ represents $C_{1-7}$-alkyl; and
- $R^3$ represents hydrogen, hydroxy, $C_{1-7}$-alkoxy, or halogen.

2. A compound according to claim 1, wherein $R^1$ represents phenyl which is optionally mono-substituted with $C_{1-7}$-alkyl or halogen; $R^2$ represents $C_{1-7}$alkyl; and $R^3$ represents hydrogen, $C_{1-7}$-alkoxy, or halogen.

3. A compound according to claim 2, wherein $R^1$ represents phenyl which is optionally mono-substituted with methyl or chloro, $R^2$ represents propyl, isopropyl or butyl, and $R^3$ represents hydrogen, methoxy, or chloro.

4. A compound according to claim 1 selected from the group consisting of:
- 5-(3-chloro-4-hydroxy-benz-(Z)-ylidene)-2-[(Z)-isopropylimino]-3-phenyl-thiazolidin-4-one,
- 5-(3-chloro-4-hydroxy-benz-(Z)-ylidene)-2-[(Z)-propylimino]-3-phenyl-thiazolidin-4-one,
- 5-(3-chloro-4-hydroxy-benz-(Z)-ylidene)-2-[(Z)-butylimino]-3-phenyl-thiazolidin-4-one,
- 5-(3-chloro-4-hydroxy-benz-(Z)-ylidene)-2-[(Z)-isopropylimino]-3-(o-tolyl)-thiazolidin-4-one,
- 5-(3-chloro-4-hydroxy-benz-(Z)-ylidene)-2-[(Z)-isopropylimino]-3-(3-chloro-phenyl)-thiazolidin-4-one,
- 5-(3-chloro-4-hydroxy-benz-(Z)-ylidene)-2-[(Z)-propylimino]-3-(o-tolyl)-thiazolidin-4-one,
- 5-(4-hydroxy-benz-(Z)-ylidene)-2-[(Z)-propylimino]-3-phenyl-thiazolidin-4-one,
- 5-(4-hydroxy-3-methoxy-benz-(Z)-ylidene)-2-[(Z)-propylimino]-3-phenyl-thiazolidin-4-one,
- 5-(4-hydroxy-benz-(Z)-ylidene)-2-[(Z)-butylimino]-3-phenyl-thiazolidin-4-one,
- 5-(4-hydroxy-3-methoxy-benz-(Z)-ylidene)-2-[(Z)-butylimino]-3-phenyl-thiazolidin-4-one,
- 5-(4-hydroxy-benz-(Z)-ylidene)-2-[(Z)-propylimino]-3-(o-tolyl)-thiazolidin-4-one, and
- 5-(4-hydroxy-3-methoxy-benz-(Z)-ylidene)-2-[(Z)-propylimino]-3-(3-chlorophenyl)-thiazolidin-4-one.

* * * * *

UNITED STATES PATENT AND TRADEMARK OFFICE
CERTIFICATE OF CORRECTION

| | | |
|---|---|---|
| PATENT NO. | : 8,263,780 B2 | Page 1 of 1 |
| APPLICATION NO. | : 12/516055 | |
| DATED | : September 11, 2012 | |
| INVENTOR(S) | : Abele et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 186 days.

Signed and Sealed this
First Day of January, 2013

David J. Kappos
*Director of the United States Patent and Trademark Office*